(12) United States Patent
Valsesia et al.

(10) Patent No.: US 12,311,039 B2
(45) Date of Patent: May 27, 2025

(54) COSMETIC COMPOSITION BASED ON JANUS PARTICLES

(71) Applicant: INTERCOS S. p. A., Milan (IT)

(72) Inventors: Patrizia Valsesia, Calco (IT); Gaetano Distefano, Bergamo (IT); Antonella Arnese, San Giuliano Milanese (IT)

(73) Assignee: INTERCOS S.P.A., Milan (IT)

( * ) Notice: Subject to any disclaimer, the term of this patent is extended or adjusted under 35 U.S.C. 154(b) by 318 days.

(21) Appl. No.: 17/253,312

(22) PCT Filed: Jun. 24, 2019

(86) PCT No.: PCT/EP2019/066649
§ 371 (c)(1),
(2) Date: Dec. 17, 2020

(87) PCT Pub. No.: WO2020/002217
PCT Pub. Date: Jan. 2, 2020

(65) Prior Publication Data
US 2021/0259927 A1 Aug. 26, 2021

(30) Foreign Application Priority Data
Jun. 27, 2018 (IT) .................. 102018000006709

(51) Int. Cl.
*A61K 8/02* (2006.01)
*A61K 8/04* (2006.01)
(Continued)

(52) U.S. Cl.
CPC ............ *A61K 8/0279* (2013.01); *A61K 8/025* (2013.01); *A61K 8/04* (2013.01); *A61K 8/893* (2013.01);
(Continued)

(58) Field of Classification Search
CPC ........ A61K 8/0279; A61K 8/025; A61K 8/04; A61K 8/893; A61K 2800/43; A61K 2800/651; A61Q 1/02; A61Q 19/00
See application file for complete search history.

(56) References Cited

U.S. PATENT DOCUMENTS

2010/0305219 A1 12/2010 Granick et al.
2016/0213578 A1* 7/2016 Schlossman ......... A61K 8/0241

FOREIGN PATENT DOCUMENTS

CN 102133802 A * 7/2011 ............... B32B 3/10
CN 106496604 3/2017
(Continued)

OTHER PUBLICATIONS

Machine translation of WO 2008154839 A1 from FIT via PE2E (Year: 2008).*
(Continued)

*Primary Examiner* — Bethany P Barham
*Assistant Examiner* — Ayaan A Alam
(74) *Attorney, Agent, or Firm* — WENDEROTH, LIND & PONACK, L.L.P.

(57) ABSTRACT

A cosmetic composition comprising Janus particles, an aqueous phase and an organic phase uses Janus particles produced with a method which includes the preparation of hollow particles (1) having two non-continuous surfaces of a material with surface energy α, of which the external one (2) is accessible and the internal one (3) is inaccessible. The surface energy of the external surface (2) is thereby modified originating particles (11) with internal surface energy α and external surface energy β. The modified particles (11) are then ground until particles are obtained constituted by small fragments (21) shaped as spherical caps with external surface (12) having modified energy and internal surface (13) having non-modified internal energy.

11 Claims, 1 Drawing Sheet

Figure 1:
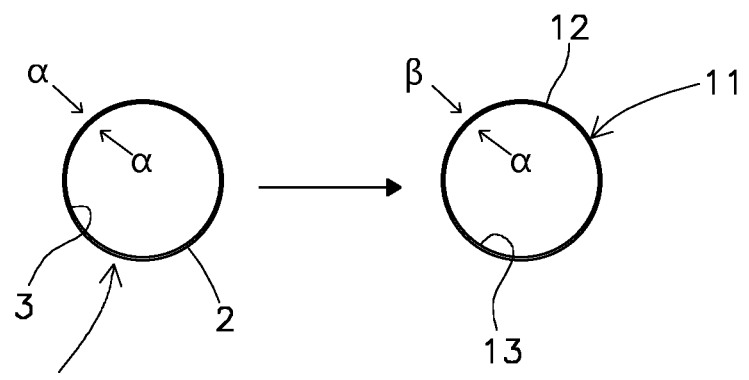

(51) Int. Cl.
  *A61K 8/893* (2006.01)
  *A61Q 1/02* (2006.01)
  *A61Q 19/00* (2006.01)
(52) U.S. Cl.
  CPC .............. *A61Q 1/02* (2013.01); *A61Q 19/00* (2013.01); *A61K 2800/43* (2013.01); *A61K 2800/651* (2013.01)

(56) References Cited

FOREIGN PATENT DOCUMENTS

| EP | 2 902 103 | 8/2015 | | |
|---|---|---|---|---|
| FR | 2956315 A1 | * | 8/2011 | ........... A61K 8/0275 |
| WO | 2008/154839 | | 12/2008 | |
| WO | 2011/088743 | | 7/2011 | |

OTHER PUBLICATIONS

Machine translation of FR 2956315 A1 from FIT via PE2E (Year: 2011).*
Machine translation provided from FIT via PE2E of CN 102133802 A (Liang et al., 2011) (Year: 2011).*
Liang, machine translation of CN-102133802-A from PE2E via FIT, 2010 (Year: 2010).*
Concave, 2016, Dictionary.com, screenshot of https://web.archive.org/web/20160523065755/https://www.dictionary.com/browse/concave (Year: 2016).*
Convex, 2016, Dictionary.com, screenshot of https://web.archive.org/web/20160503144101/https://www.dictionary.com/browse/convex (Year: 2016).*
International Search Report (ISR) issued Jan. 2, 2020 in International (PCT) Application No. PCT/EP2019/066649.
International Preliminary Report on Patentability (IPRP) issued Aug. 6, 2020 in International (PCT) Application No. PCT/EP2019/066649.
Written Opinion of the International Preliminary Examining Authority issued May 28, 2020 in International (PCT) Application No. PCT/EP2019/066649.
Database WPI, Week 200918, Thomson Scientific, London, GB; AN 2009-B48219, XP002789748, & WO 2008/154839 A1 (Chinese Acad Sci Chem Inst), Dec. 24, 2008.
Database WPI, Week 201154, Thomson Scientific, London, GB; AN 2011-J58980, XP002789749, & WO 2011/088743 A1 (Chinese Acad Sci Chem Inst), Jul. 28, 2011.
Database WPI, Week 201734, Thomson Scientific, London, GB; AN 2017-19187J, XP002789750, CN 106 496 604 A (Univ Liaoning), Mar. 15, 2017.
Jing Hu et al., "Fabrication, properties and applications of Janus particles", Chemical Society Reviews, vol. 41, No. 11, pp. 4356-4378, XP055126231, ISSN: 0306-0012, DOI: 10.1039/c2cs35032g, Jun. 1, 2012.

* cited by examiner

COSMETIC COMPOSITION BASED ON JANUS PARTICLES

The present invention relates to a cosmetic composition based on Janus particles.

The invention generally relates to the manufacturing of amphiphilic particles having the ability to mechanically stabilize the interface between two immiscible liquids, whereby forming a stabilized emulsion without the use of molecular emulsifiers. Said stabilized emulsions are named "Pickering emulsions" in academic literature and are known to form thermodynamically stable emulsions.

It is also known that the stability of Pickering emulsions, when obtained using so-called Janus particles, greatly exceeds that of the emulsions obtained by molecular emulsifiers.

A growing number of cosmetic products contain water as one of the main ingredients for economic and sustainability reasons, as well as for the feeling of freshness typical of such formulations. Many of them consist of water-in-oil emulsions (silicone) or oil (silicone)-in-water emulsions. The emulsions feature the presence of two immiscible phases, in which one phase is dispersed in the other and the dispersed phase is usually stabilized with emulsifiers and co-emulsifiers. The emulsifiers are amphiphilic molecules and can be of various nature (ionic or non-ionic) with variable molecular weight, often below 1000 Da. It is known that the droplet size of the dispersed phase is a fundamental property which has an impact on the appearance, the sensory properties and the stability of the emulsion itself.

Pickering emulsions instead are based on solid materials which have a contact angle of about 90° with the two liquids involved in the emulsion. This means that the material will be wetted independently by either one or the other liquid: once finely divided into powder form, this material will be adsorbed at the interfaces between the two liquids, remaining sequestered therein. As final result, all interfaces will be covered by particles which will stabilize the emulsion against flocculation and coalescence. This effect can be obtained only by appropriately choosing the liquid phases and the concerned materials. The interfacial energy between a solid and a liquid may be defined as the sum of the energy contributions between the liquid molecules and the chemical functions exposed on the surface of the solid: said contributions may be classified as polar, dispersive (Van der Waals), acid-base, mediated by hydrogen bonds, etc. Amphiphilic surfaces have affinity for water and oils, i.e. possess surface properties which determine interfacial energies, respectively with water and oil, of comparable entity: the solid thus has no preferences to be wetted either by the water or by the oil. By finely dividing said material in powder form, it can act as an emulsifier because the solid particles will migrate to the water-oil interface, mechanically preventing the dispersed phase from coalescing. The surface properties of such materials are homogeneous, but amphiphilic materials are rare and difficult to design. It is thus apparent that a given material powder will act as a solid emulsifier for a restricted field of immiscible liquids (surface tensions) and consequently the method cannot be easily generalized to every type of formulation.

This problem may be overcome by using Janus particles, i.e. particles having distinct faces (e.g. hydrophobic and hydrophilic), each preferably wetted by one of the two phases (e.g. oils and water).

Janus particles take their name from the two-faced Ancient Roman deity and are an evolution of amphiphilic particles as defined above. Said Janus particles have surfaces with different chemical affinity (surface energy) according to the zones of the particle itself. For example, flake Janus particles may feature a hydrophilic surface and a hydrophobic surface. Janus particles are better than powder emulsifiers with homogeneous surface energy (not in compartments) because the interaction with the liquid phases in an emulsion is specific: the hydrophilic face interacts with the aqueous phase, while the hydrophobic face interacts with the oil (or silicone) phase. As a result, the particles migrate to the liquid-liquid interface and are irreversibly segregated therein. Janus particles can be manufactured by using various techniques, described in the literature, but all having in common a low yield and many steps of manufacturing.

Indeed, Janus particles today (see references listed below) are manufactured using sophisticated methods and low yields which cannot be executed efficiently or cost-effectively. Therefore, to the best of our knowledge, Janus particles are not available on the market among the ingredients used in the cosmetic field nor in other industrial fields today.

In this regard, the following bibliographical references may be cited:

1) Chariya Kaewsaneha et al., "Preparation of Janus Colloidal Particles Via Pickering Emulsion: An Overview", Colloids and Surfaces A: Physiochemical and Engineering Aspects—Volume 439, 20 Dec. 2013, pages 35-42.
2) Yunoi Yang et al., "An Overview of Pickering Emulsions: Solid-Particle Materials, Classification, Morphology, and Applications", Frontiers in Pharmacology, 1 May 2017, Volume 8, Article 287.
3) Fuxin Liang et al., "Rational Design and Synthesis of Janus Composites", Advanced Materials, Volume 26, Part 40, 29 Oct. 2014, pages 6944-6949.
4) Yoshimune Nonomura et al., "Adsorption of Disk Shaped Janus Beads at Liquid-Liquid Interfaces", Langmuir, 2004, 20, 11821-11823.
5) B. P. Binks et al., "Particles Adsorbed at the Oil-Water Interface: Theoretical Comparison between Spheres of Uniform Wettability and "Janus" Particles", Langmuir, 2001, 17, 4708-4710.
6) Jie Wu et al., "Recent Studies of Pickering Emulsions: Particles Make the Difference", Small, Volume 12, Part 34, 14 Sep. 2016, pages 4633-4640.

The present invention provides a specific manufacturing method for making Janus particles usable for cosmetic use. The material is non-nanometeric (in comparison with the non-Janus solid emulsifiers present on the market) and therefore does not pose any safety problems for consumers.

According to the present invention, Janus particles are used with the function of "solid emulsifiers" in cosmetic formulations, originating emulsions which may have the appearance of classical emulsions or, as a function of the formulation itself, may feature special visual and sensory effects, both in mass and during application (e.g. stable macroemulsions with drops of the dispersed phase visible to the naked eye). These new product types have great advantages, among which is the absence of traditional molecular emulsifiers which can be aggressive on the skin. Indeed, skincare and makeup products require, in particular, to improve and in all cases respect skin physiology: for this reason, emulsions without traditional emulsifiers represent a considerable improvement in the art.

Furthermore, the exceptional stability of such emulsions may pave the way for new emulsions characterized by a low viscosity.

It is the main object of the present invention to provide a cosmetic composition which uses a new method for manufacturing Janus particles which can be used for emulsions directed to making cosmetic products, which can be easily performed with ordinary equipment at low production costs. Furthermore, the new method of manufacturing Janus particles according to the present invention allows the yields of tens of kilograms per hour. It is another object of the present invention the use of such Janus particles in the formulation of cosmetic products for face, eye, lip or body makeup and for skincare.

Various techniques may be used to modify the surface energy of the materials in the prior art. Said methods, if applied to materials in powder form, modify the surface in a non-specific manner, i.e. by modifying all surfaces accessible to the treatment (either chemical or physical). "Physical treatment" means the deposition of a layer of material the molecules of which are not covalently bound to the surface, e.g. by precipitation or casting from the solvent. "Chemical treatment" instead refers to the deposition of a layer of material, the molecules of which are covalently bound to the surface. Both types of treatment alter the surface energy of the original surface, however the physical treatment may be removed by separation methods (e.g. by extraction), while the chemical method requires the decomposition of the covalent bond formed between the treating agent and the surface itself and is therefore more stable.

It is possible to transform a hydrophilic surface into a hydrophobic one, e.g. using well-known chemical functionalization techniques (chemical sol-gel): in the case of the techniques used in the prior art, it is not possible to define with precision the area of a particle to be modified to achieve functionalization in compartments and the entire surface is normally modified. It would be necessary to screen part of the surface of the particles from surface modification. Said screening methods are described in the literature but employ wet techniques and have low yields.

Powder materials having the morphology of hollow spheres (spherical bubbles) are inherently self-screened. Two surfaces can be distinguished in each particle: an inner surface, not accessible to the treatment, and an outer surface, accessible to the treatment.

A method according to the present invention functionalizes the outer surface of said particles with any of the methods known in the prior art. After functionalization, the particles will conceal a "protected", non-functionalized, surface and an exposed functionalized surface. The Janus particles are finally obtained by grinding said materials so as to expose the non-functionalized surfaces. If the starting material has a hollow sphere morphology, after treatment and grinding it is possible to obtain particles in the form of spherical cap.

There are many different materials having microbubble morphology on the market. A category is constituted by glass (e.g. Glass Microbubbles made by 3M). Another example is constituted by hollow microspheres made of plastic material (e.g. Expancel made by Akzo Nobel). However, any material in powder form which features internal and external surfaces (bubbles or shells) may be used in the present invention. This class of materials is increasingly available on the market; indeed, they have the function of functional excipients to obtain formulations with extremely low specific weight.

The cosmetic composition according to the invention is defined in claim 1.

The method used for manufacturing Janus particles which can be used for the cosmetic composition according to the invention consists in the following succession of phases, illustrated in accompanying FIGS. 1 and 2.

Figure 2:
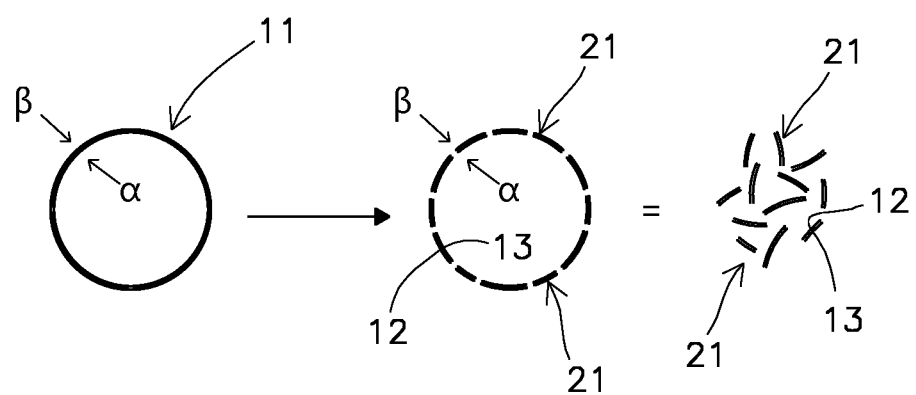

1) Starting from hollow particles 1 (e.g. in form of spherical bubble, as shown on the left in FIG. 1) which feature two non-continuous surfaces, an external (accessible) one 2 and an internal (non-accessible) one 3, of a given material with surface energy α (e.g. a hydrophilic material having contact angle with water $W_{CA}$-α<90° or a hydrophobic material having angle $W_{CA}$-α>90°), the surface energy of the external surface is chemically or physically changed (e.g. by chemical coating) originating modified particles 11, such as the one shown on the right in FIG. 1. The hollow particles obtained 11 feature an outer surface 12 modified with surface energy β (greater or lower than α) having different contact angle with water ($W_{CA}$-β>$W_{CA}$-α or $W_{CA}$-β<$W_{CA}$-α) and an inner surface 13 not modified with original surface energy α because the internal surface was not accessible for the modification. The surface treating agent can be, e.g. a copolymer of polymethylhydrogensiloxane or a triethoxy- and/or trimethoxy-silane. In the case of physical modification, it can be made for deposition of a modifying material, by evaporation of a volatile solvent or by deposition of molten material and subsequent solidification.

2) The particles 11 (shown on the left in FIG. 2) are then ground with any grinding technique capable of breaking them (central part in FIG. 2) to obtain small fragments in form of spherical caps (particles 21). The lower the solid angle described by the caps, the greater the approximation of the caps to a planar shape. The breakage of treated hollow spheres will make accessible the non-modified internal surface 13, whereby generating the Janus particles (right side in FIG. 2).

By using the Janus particles made according to such method it is possible to obtain a cosmetic composition comprising an aqueous phase and an organic phase, in which the Janus particles are comprised between 0.01% by weight and 99.99% by weight and the sum of aqueous phase and organic phase is between 0.01% by weight and 99.99% by weight.

In particular, a cosmetic composition can be obtained in which the organic phase is comprised between 10% and 90% by weight. The aqueous phase is comprised between 90% by weight and 10% by weight and the Janus particles are comprised between 20% by weight and 0.01% by weight, and in which the aqueous phase is dispersed in the organic phase (water-in-oil/silicone emulsion) or vice versa (oil/silicone-in-water emulsion). A cosmetic composition may also be obtained in which the organic phase is comprised between 0.01% by weight and 10% by weight, the aqueous phase is comprised between 10% by weight and 70% by weight and the Janus particles are comprised between 10% by weight and 90% by weight.

The aqueous phase can be constituted by water and hydro-soluble and/or hydro-dispersible substances, while the organic phase may be constituted by oils belonging to the class of triglycerides and/or esters and/or glyceryl esters and/or silicones and/or any other oils acceptable from the cosmetic point of view and respective mixtures thereof and may contain one or more oils and oil-soluble and/or oil-dispersible substances.

FORMULATION EXAMPLES

Some examples are shown below related to the preparation of Janus particles according to the invention and their use for making emulsions and other preparations suited for cosmetic applications.

Example 1—Preparation of Janus Particles (Hydrophilic-Silicone) Functionalized with Dimethicone from Hollow Particles of Hydrophilic Glass In a powder mixer, 200 grams of hollow glass particles having an average diameter of 100 microns are added and gently mixed at 100 rpm for 5 minutes. After the addition of a surface treatment agent (copolymer of polymethylhydrogensiloxane-polydimethylsiloxane, 4 grams), the mixture is further stirred for 5 minutes. The mixture thus obtained is thermally treated at 150° C. in air for 24 hours. After the thermal treatment, the mixture is allowed to cool. The coated hollow particles have a surface energy lower than 33 dyn/cm. The particles are then milled using an air-jet grinder with a feed rate of 10 g/min at 7 bars (injection and grinding chamber). The final distribution of particle size is between 0.1 and 20 microns, as measured by means of a laser diffraction granulometer.

Example 2—Preparation of Janus Particles (Hydrophilic-Aliphatic) Functionalized with Behenylcarbamoylpropyl Polysilsesquioxane from Hollow Particles of Hydrophilic Glass In a heated powder mixer, 200 grams of hollow glass particles having an average diameter of 200 microns are added and gently mixed at 60 rpm for 5 minutes: after adding 4 grams of behenylcarbamoylpropyl triethoxysilane surface treating agent, the mixture is taken to 80° C. during mixing and mixed completely for 1 hour. 1 gram of an aqueous solution of diluted acid is introduced into the mixer as catalyst and mixing is continued for 2 hours at 80° C. The mixture is then left to cool. The coated hollow particles have a surface energy lower than 33 dyn/cm. The particles are then subjected to intensive mixing at 3000 rpm to break the hollow shells in-situ to achieve a final distribution of particle sizes ranging between 0.1 and 20 microns.

Example 3—Preparation of Janus Particles (Hydrophilic-Aliphatic) Functionalized with Triethoxycaprylylsilane from Hollow Particles of Hydrophilic Glass In a heated powder mixer, 200 grams of hollow glass particles having an average diameter of 200 microns are added and gently mixed at 60 rpm for 5 minutes: after adding 4 grams of triethoxycaprylylsilane surface treating agent, the mixture is taken to 80° C. during mixing and mixed completely for 1 hour. 1 gram of an aqueous solution of diluted acid is introduced into the mixer as catalyst and mixing is continued for 2 hours at 80° C. The mixture is then left to cool. The coated hollow particles have a surface energy lower than 33 dyn/cm. The particles are then milled using an air-jet grinder at a feed rate of 10 g/min at 7 bars (injection and grinding chamber). The final distribution of particle size is between 0.1 and 10 microns.

Example 4—Preparation of Janus Particles (Hydrophobic and Hydrophilic) Functionalized by Means of Atmospheric Plasma from Hollow Hydrophobic Polymer Particles In an atmospheric plasma reactor, 200 grams of hollow spheres of hydrophobic polymer (polyacrylonitrile/cross-linked polymethyl methacrylate), having average particle size of 80 microns, are added and subjected to treatment for 2 hours. The treated powder becomes hydrophilic with a surface energy greater than 72 dyn/cm. The powder is further milled to break the shells using an air-jet mill at low temperature (under the glass transition temperature of the material) whereby generating the Janus particles. The final distribution of particle size is between 0.1 and 10 microns.

Example 5—Preparation of Water-In-Silicone Emulsion Using the Janus Particles of Example 1

| COMPONENTS | WEIGHT % |
|---|---|
| Phase A | |
| Janus particles (Example 1) | 5.0 |
| Dimethicone | 75.0 |
| Phase B | |
| Water | 20.0 |

The water-in-silicone emulsion is obtained by preparing Phase A in a beaker at room temperature under mechanical agitation and adding Phase B while generating the emulsion with a high-shear rotor-stator apparatus at 10000 rpm for 5 minutes. The final distribution of the water droplets is between 10 and 150 micron, as detected under optical microscopy. The obtained emulsion is stable against coalescence for more than κ months at room temperature.

Example 6—Preparation of Water-In-Oil Emulsion Using the Janus Particles of Example 2

| COMPONENTS | WEIGHT % |
|---|---|
| Phase A | |
| Janus particles (Example 2) | 5.0 |
| Isohexadecane | 45.0 |
| Phase B | |
| Water | 50.0 |

The water-in-oil emulsion is obtained by preparing Phase A in a beaker at room temperature under mechanical agitation and adding Phase B while generating the emulsion with a high-shear rotor-stator apparatus at 10000 rpm for 5 minutes. The final distribution of the water droplets is between 10 and 170 micron, as detected under optical microscopy. The obtained emulsion is stable against coalescence for more than 6 months at room temperature.

Example 7—Preparation of Silicone-In-Oil Emulsion Using the Janus Particles of Example 4

| COMPONENTS | WEIGHT % |
|---|---|
| Phase A | |
| Water | 65.0 |
| Janus particles (Example 4) | 5.0 |
| Phase B | |
| Silicone | 30.0 |

The water-in-oil emulsion is obtained by preparing Phase A in a beaker at room temperature under mechanical agitation and adding Phase B while generating the emulsion with a high-shear rotor-stator apparatus at 10000 rpm for 5 minutes. The final distribution of the water droplets is between 30 and 200 micron, as detected under optical microscopy. The obtained emulsion is stable against coalescence for more than 6 months at room temperature.

Example 8—Preparation of Water-In-Silicone Emulsion with In-Situ Generation of Janus Particles (Humid Grinding)

| COMPONENTS | WEIGHT % |
|---|---|
| Phase A | |
| Glass bubbles treated with silicone | 5.0 |
| Dimethicone | 40.0 |
| Phase B | |
| Dimethicone | 35.0 |
| Phase C | |
| Water | 20.0 |

The example shows the case in which the Janus particles are generated in-situ during the production of the emulsion. The glass microbubbles treated with silicone of Example 1 are used as such before grinding. Phase A is prepared in a beaker and calendered in form of mixture into a three-cylinder grinder (calender) by means of which the Janus particles in silicone dispersion are generated. Thus, Phase A is added to Phase B at room temperature and then Phase C is added during the generation of the emulsion with high-shear rotor-stator apparatus at 10000 rpm for 5 minutes. The final distribution of the water droplets is between 10 and 150 micron, as detected under optical microscopy. The obtained emulsion is stable against coalescence for more than 6 months at room temperature.

Example 9—Preparation of Foundation in Water-In-Oil Emulsion

| COMPONENTS | WEIGHT % |
|---|---|
| Phase A | |
| Oils and emollients | 35.0 |
| Waxes | 10.0 |
| Phase B | |
| Janus particles (Example 1) | 5.0 |
| Hydrophobic pigments | 8.5 |
| Phase C | |
| Water | 40.0 |
| Preservatives | 1.0 |
| Phase D | |
| Antioxidants | 0.5 |

The foundation in water-in-oil emulsion is manufactured as follows. Phase A is taken to 80° C. until the wax melts. Then Phase B is added under mechanical agitation. Phase C is heated to 80° C. and added to Phase A+B during the generation of the emulsion with high-shear rotor-stator apparatus at 10000 rpm for 5 minutes. Then Phase D is added to the mixture under agitation. The temperature is then lowered to ambient temperature under mechanical agitation.

Example 10—Preparation of a "Powder-Cream" Cosmetic Product

| COMPONENTS | WEIGHT % |
|---|---|
| Phase A | |
| Janus particles (Example 1) | 10.0 |
| Hydrophobic pigments | 10.0 |
| Hydrophobic excipients | 10.0 |
| Phase B | |
| Dimethicone | 6.0 |
| Phase C | |
| Water | 63.7 |
| Preservatives | 0.3 |

The "power-cream" product is made as follows. Phase A is mixed in a powder mixer at ambient temperature (2500 rpm for 5 min). Phase B is added to Phase A and further mixed homogeneously (two cycles at 2500 rpm for 5 min). Phase C is then added to Phase A+B and the mixture is mixed until the mass acquires the appearance of a flowing dry powder. Such powder possesses the ability to turn into a cream during application (friction) on the skin and return dry following the evaporation of the water.

Example 11—Preparation of an Oil-In-Water Emulsion for Skincare

| COMPONENTS | WEIGHT % |
|---|---|
| Phase A | |
| Water | 60.0 |
| Humectants | 7.0 |
| Preservatives | 1.0 |
| Rheological modifier | 1.0 |
| Janus particles (Example 4) | 5.0 |
| Phase B | |
| Oils and emollients | 25.0 |
| Phase C | |
| Antioxidants | 0.5 |
| Phase D | |
| Active principles | 0.5 |

The oil-in-water emulsion for skincare is made as follows. Phase A is taken to 50° C. until it is homogeneous. Then Phase C is heated to 50° C. Phase B is added to Phase A during the generation of the emulsion with high-shear rotor-stator apparatus at 10000 rpm for 5 minutes. Then the emulsion is left to cool and Phases C and D are then added with mechanical agitation (200 rpm).

Comparative Example

A comparative example is provided below which demonstrates the failure of the attempt to form water-in-silicone emulsions using particles obtained with different manufacturing methods (no treatment, no grinding or different treatment-grinding order), Comparative powders are described as follows:

Comparative Example I (hydrophilic microbubbles)—Powder in hydrophilic hollow glass spheres, used as such (no coating, no grinding)

Comparative Example II (hydrophilic flakes)—Hydrophilic flakes are obtained as in Example 1 without step of coating (no coating, with grinding)

Comparative Example III (hydrophobic microbubbles)—Hollow hydrophobic glass spheres, obtained as in Example 1 without step of air-jet grinding (with coating, no grinding)

Comparative Example IV (hydrophobic flakes)—Hydrophobic flakes are obtained as in Example 1 by inverting the coating/grinding order (with grinding, with coating)

The emulsions are prepared in accordance with Example 5 with the different powders (Comparative Examples I-IV) used as Phase A. Phase B (aqueous phase) is added with 0.1% of water-soluble dye FD&C Blue1 to color the water droplets.

The visual and optical microscopy evaluation show that only Janus particles as described in the present invention generate Pickering emulsions with improved stability. No emulsion is formed when the particles are completely hydrophilic (hollow spheres or flakes) or when hollow hydrophobic spheres are used (Comparative Example I, Comparative Example II and Comparative Example III, respectively). Hydrophobic flakes (Comparative Example IV) lead to a Pickering emulsion based on an intermediate mean wetting between the aqueous phase and the silicone phase: however, such emulsions show a coarser droplet size and a lower stability against coalescence, as demonstrated by an accelerated stability test (in centrifuge at 4000 rpm for 2 minutes or 2500 rpm for 10 min) compared to the Pickering emulsion based on Janus particles which is the object of the present invention.

The invention claimed is:

1. A cosmetic composition, comprising:
   Janus particles comprising a concave surface having a non-modified surface energy $\alpha$ and a convex surface having a modified surface energy $\beta$,
   an aqueous phase, and
   an organic phase,
   wherein the cosmetic composition comprises between 0.01% by weight and 99.99% by weight of the Janus particles, and the cosmetic composition comprises between 0.01% by weight and 99.99% by weight of the sum of the aqueous phase and the organic phase, and
   wherein the Janus particles are obtained by a process comprising:
   chemically treating original hollow spherical particles comprising a concave surface having a surface energy $\alpha$ and a convex surface having the same surface energy $\alpha$, the chemical treating being made with one chemical treatment agent, to obtain modified hollow spherical particles comprising the concave surface having the non-modified surface energy $\alpha$ and the convex surface having the modified surface energy $\beta$, and
   grinding the modified hollow spherical particles to obtain the Janus particles comprising the concave surface having the non-modified surface energy $\alpha$ and the convex surface having the modified surface energy $\beta$,
   wherein the process does not comprise a chemical treatment of the Janus particles after the grinding, and
   wherein the one chemical treatment agent is selected from the group consisting of (1) a copolymer of polymethylhydrogensiloxane and (2) behenylcarbamoylpropyl triethoxysilane.

2. The cosmetic composition according to claim 1, wherein the aqueous phase comprises water and at least one substance selected from the group consisting of a hydrosoluble substance and a hydro-dispersible substance.

3. The cosmetic composition according to claim 1, wherein the organic phase comprises at least one oil belonging to the triglyceride and/or ester and/or glyceryl ester class and/or silicones and/or any other oils acceptable for cosmetic use and respective mixtures thereof.

4. The cosmetic composition according to claim 1, wherein the organic phase comprises at least one oil and an oil-soluble and/or oil-dispersible substance.

5. The cosmetic composition according to claim 1,
   comprising between 10% by weight and 90% by weight of the organic phase, between 90% by weight and 10% by weight of the aqueous phase, and between 20% by weight and 0.01% by weight of the Janus particles, and
   wherein the aqueous phase is dispersed in the organic phase as a water-in-oil/silicone emulsion, or the organic phase is dispersed in the aqueous phase as an oil/silicone-in-water emulsion.

6. The cosmetic composition according to claim 1, comprising between 0.01% by weight and 10% by weight of the organic phase, between 10% by weight and 70% by weight of the aqueous phase, and between 10% by weight and 90% by weight of the Janus particles.

7. The cosmetic composition according to claim 1, wherein the hollow spherical particles are shaped as spherical bubbles.

8. The cosmetic composition according to claim 1, wherein the non-modified surface energy $\alpha$ is higher than the modified surface energy $\beta$.

9. The cosmetic composition according to claim 1, wherein the non-modified surface energy $\alpha$ is lower than the modified surface energy $\beta$.

10. The cosmetic composition according to claim 1, wherein the one chemical treatment agent is a copolymer of polymethylhydrogensiloxane.

11. The cosmetic composition according to claim 1, wherein the one chemical treatment agent is behenylcarbamoylpropyl triethoxysilane.

* * * * *